United States Patent [19]

Hunds

[11] Patent Number: 5,525,724
[45] Date of Patent: Jun. 11, 1996

[54] PROCESS FOR THE PREPARATION OF CHLOROPYRIMIDINES

[75] Inventor: Artur Hunds, Bonn, Germany

[73] Assignee: Huels Aktiengesellschaft, Marl, Germany

[21] Appl. No.: 394,750

[22] Filed: Feb. 27, 1995

[30] Foreign Application Priority Data

Mar. 12, 1994 [DE] Germany .......................... 44 08 404.8

[51] Int. Cl.⁶ ................................................. C07D 239/30
[52] U.S. Cl. ........................ 544/334; 544/300; 544/303; 544/310; 544/313; 544/315; 544/311; 544/312; 544/316; 544/317; 544/318; 544/319; 544/320; 544/321; 544/323; 544/324; 544/325; 544/326; 544/328; 544/329; 544/330; 544/331; 544/332; 544/333
[58] Field of Search .................................... 544/334, 300, 544/313, 312, 318, 321, 325, 329, 332

[56] References Cited

U.S. PATENT DOCUMENTS 3,845,194  10/1974  Somlo et al. .......................... 423/300

Primary Examiner—John M. Ford
Attorney, Agent, or Firm—Oblon, Spivak, McClelland, Maier & Neustadt

[57] ABSTRACT

A process for the preparation of chloropyrimidines of the formula

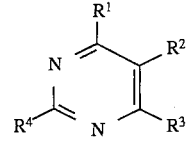

in which the substituents may be alkyl, cycloalkyl, aryl or radicals containing heteroatoms, but in which at least one of the substituents $R^1$ to $R^4$ must be Cl, which involves:

reacting a hydroxy-pyrimidine or its tautomeric keto form with phosphoryl chloride in the presence of an amine or amine hydrochloride;

recovering phosphoryl chloride after the reaction by adding phosphorus pentachloride and distilling the phosphoryl chloride; and separating the chloropyrimidine from the amine hydrochloride by addition of a solvent which will dissolve the chloropyrimidine but not the amine hydrochloride and removing the amine hydrochloride.

9 Claims, No Drawings

PROCESS FOR THE PREPARATION OF CHLOROPYRIMIDINES

BACKGROUND OF THE INVENTION

1. Field of the Invention

The present invention relates to an improved process for the preparation of chloropyrimidines.

2. Discussion of the Background

Chloropyrimidines are of great commercial interest as intermediates for new, highly effective pesticides and pharmaceuticals. In many methods for the preparation of chloropyrimidines, amines, preferably N,N-dimethylaniline or N,N-diethylaniline, or amine hydrochlorides are added in accordance with the procedures outlined in D. J. Brown, The Pyrimidines, 162–167 (1962) in order to improve yields. In this conventional process, after removal of the excess $POCl_3$ by distillation, the resulting reaction mixture is taken up in ice-water and the chloropyrimidine is extracted from the aqueous phase or removed by filtration.

However, this process can not be used for the preparation of relatively large quantities on an industrial scale due to the high risk of uncontrollable heat generation during the aqueous work-up. Also, flocculent and slimy byproducts from the reaction render the extraction and filtration of the products from the aqueous phase difficult, and some chloropyrimidines are readily decomposed in water. A particular disadvantage, however, is the fact that large quantities of effluent are obtained which contain a very high quantity of phosphoric acid, amine hydrochlorides and other toxic by-products from the reaction.

If attempts are made to work up the reaction mixture by distillation once the $POCl_3$ has been removed, severe decomposition of the chloropyrimidines and decomposition or sublimation of the amine hydrochlorides are observed, especially in the case of large batches. Furthermore, there remain large quantities of highly viscous residues which contain polymeric phosphorus compounds and other decomposition products. Disposal of these polymeric and other decomposition products is difficult, making this work-up procedure also unusable for the industrial preparation of relatively large quantities of chloropyrimidines.

A substantial improvement to the process for preparing chloropyrimidines is described in DE-A-22 48 747, which discloses that the polymeric phosphorus compounds, which are obtained as by-products of many reactions involving $POCl_3$ or $POBr_3$, are converted back to $POCl_3$ or $POBr_3$, respectively, using phosphorus pentahalides, which may also be produced in situ. Removal of the phosphoryl halides, by distillation, leaves the reaction product together, if appropriate, with the catalyst used. If this process is applied to the preparation of chloropyrimidines, then the distillative removal of the excess $POCl_3$ leaves a mixture of the chloropyrimidine and the amine hydrochloride. In DE A-22 48 747, such a mixture is taken up in water and acid at from 60° to 80° C., the product is separated off and the amine is liberated from the aqueous phase by adding sodium hydroxide solution and extracting with toluene. The extracts are then fractionally distilled to recover about 68% of the amine.

However, this process also has great disadvantages. Here too the presence of flocculent, slimy by-products, which are difficult to remove by filtration, makes the separation of the product from the aqueous phase extremely difficult, even when solvents are added for extraction. Also, in the case of relatively sensitive chloropyrimidines, there is the risk of decomposition by hydrolysis. The complicated recovery of the amine by addition of sodium hydroxide solution followed by extraction from the aqueous phase is likewise hindered by poor phase separation, and tends to leave behind an aqueous phase which still contains residues of toxic, chlorinated organic compounds and amines which are toxic and not readily degradable.

The work-up method disclosed in DE A-22 48 747, involves the distillative removal of the phosphoryl chloride, followed directly by distillation of the product. However this work-up is unsuccessful when amine or amine hydrochloride is present in the reaction mixture. In such cases, severe encrustation and decomposition are observed even when vacuum distillations are employed.

SUMMARY OF THE PRESENT INVENTION

Accordingly, one object of the present invention is to provide a process for the preparation of chloropyrimidines on an industrial scale, which is suitable for separating the chloropyrimidine/amine hydrochloride reaction mixture, which avoids a difficult phase separation and which does not produce effluents which are toxic and not readily degradable.

This object and others have been satisfied by the discovery of a process for the preparation of chloropyrimidines; comprising:

reacting a hydroxy-pyrimidine or its tautomeric keto form with phosphoryl chloride in the presence of an amine or amine hydrochloride;

recovering phosphoryl chloride after the reaction by adding phosphorus pentachloride and distilling the phosphoryl chloride; and separating the chloropyrimidine from the amine hydrochloride by addition of a solvent which will dissolve the chloropyrimidine but not the amine hydrochloride and removing the amine hydrochloride.

DETAILED DESCRIPTION OF THE PREFERRED EMBODIMENTS

The present invention relates to an improved process for the preparation of chloropyrimidines of the formula

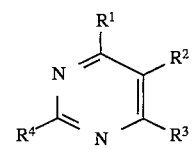

wherein the substituents $R^1$, $R^2$, $R^3$ and $R^4$ are hydrogen, unsubstituted or substituted alkyl, cycloalkyl, aryl, heteroaryl, $OR^5$, $SR^5$, $NH_2$, $NHR^5$, $N(R^5)_2$, NO $NO_2$, COOH, $COOR^5$, CN or halogen, where $R^5$ may be unsubstituted or substituted alkyl, cycloalkyl, aryl or heteroaryl but at least one of the substituents $R^1$ to $R^4$ must be Cl.

These chloropyrimidines are prepared from hydroxypyrimidines or their tautomeric keto forms and phosphoryl chloride ($POCl_3$) often with the addition of an amine or amine hydrochloride. The phosphorus compounds which are produced during the reaction are removed by an aqueous workup procedure or are converted back using phosphorus pentachloride into phosphoryl chloride, which is then distilled.

The solvent can be added before, during or after the distillative removal of the $POCl_3$, and is preferably added after the distillation of the $POCl_3$. In the case of relatively volatile and low-melting chloropyrimidines, such as 4,6- dichloropyrimidine, it is advantageous to first remove the majority of the excess POCl$_3$ by distillation, then to add the solvent to the resulting amine hydrochloride/chloropyrimidine mixture at room temperature or elevated temperature.

In the case of nonvolatile chloropyrimidines or those of low volatility, this procedure may result in the batch crystallizing and becoming unstirrable during the distillative removal of the excess POCl$_3$. In such a case, it is advantageous to add the solvent during or even before the distillation of the excess POCl$_3$ at room temperature or elevated temperature. The remaining amine hydrochloride is then removed at room temperature or elevated temperature by a liquid-solid separation process such as filtration or centrifugation. The chloropyrimidine can be isolated from the resulting solution by conventional methods, such as distillation, sublimation, crystallization or chromatography.

In the case of sensitive chloropyrimidines or those which can be readily sublimed, such as 4,6-dichloropyrimidine, the following procedure is recommended for further purification: In the extraction, a solvent or solvent mixture is used which has a boiling point similar to that of the chloropyrimidine and the extracts obtained after removal of the amine hydrochloride by filtration are distilled. The solvent which is co-distilled with the chloropyrimidine prevents crystallization of the chloropyrimidine in the apparatus, and the resulting distillate is a solution which is largely free from residual phosphorus oxides and POCl$_3$. Other distillation variants are also possible, for such as distillation using thin-film or falling-film evaporators.

In order to prevent encrustation at the bottom of the distillation port during distillation, it is preferred to add distillation auxiliaries, such as high-boiling liquids or low-melting solids. Examples of such distillation auxiliaries include commercially available polyethylene glycols and polyethylene glycol ethers, and also high-boiling carboxylic esters such as diethyl phthalate, carbonates such as diphenyl carbonate and esters of inorganic acids, such as triphenyl phosphate.

It has been found that the amine hydrochloride removed by filtration, after a brief drying operation to remove adherent solvent residues if desired, can be employed directly in further batches. Conversion of the amine hydrochloride back to the free amine is not necessary.

Suitable solvents for the process of the present invention are liquids which act as good solvents for chloropyrimidines and poor solvents for amine hydrochlorides, and which react only minimally with the product mixture. They should also be able to be separated and recovered readily by distillation from the chloropyrimidine and from any phosphorus oxide and phosphoryl chloride residues which may be present. Examples of suitable solvents include esters having a total of 2 to 10 carbon atoms such as methyl and ethyl acetate, methyl and ethyl benzoate, paraffinic hydrocarbons of 6 to 14 carbon atoms such as n-hexane, cyclohexane or decalin, aromatic hydrocarbons of 6 to 14 carbon atoms such as xylenes, mesitylene or tetralin, halogenated hydrocarbons of 1 to 6 carbon atoms such as 1-chlorobutane or trichloroethane, or ethers of 4 to 12 carbon atoms such as tert-butyl methyl ether, di-n-butyl ether or mixtures thereof. However, many other suitable solvents are available and are expressly not to be excluded.

As the additive for increasing the chloropyrimidine yield, it is possible to use any amine or amine hydrochloride or a quaternary ammonium salt, N(R$^6$)$_4$$^+$Cl, or mixtures thereof, provided the additive is sufficiently soluble in POCl$_3$ and is inert under the reaction conditions. The hydrochlorides of aliphatic amines, such as ethylamine hydrochloride and dibutylamine hydrochloride, are particularly preferred. Most preferred are the tertiary aliphatic amines N(R$^6$)$_3$ and their hydrochlorides. In the context of the present invention, R$^6$ may be straight-chain or branched alkyl of 1 to 8 carbon atoms or cycloalkyl of 5 to 8 carbon atoms. Examples of suitable tertiary aliphatic amines include triethylamine and trimethylamine.

In accordance with the process of the present invention, the amines or amine hydrochlorides are preferably used in quantities of from 0.1 to 2.0 mol per mol of hydroxypyrimidine. The amine hydrochlorides of the present invention crystallize better and are more resistant to heat than the hydrochlorides of N,N-dimethylaniline and N,N-diethylaniline, which according to D. J. Brown (supra) are the most commonly used. The amine hydrochlorides of the present invention can therefore be filtered more readily and recovered in better yields with higher purities. One advantage of the present process therefore resides in the omission of the problematic separation of the aqueous phase from the product phase and the production of no toxic effluent.

An additional advantage is that POCl$_3$ and the solvent used for the extraction can be recovered in high yields. By simple filtration and, if desired, a brief drying operation the amine can be recovered in high yield as its hydrochloride and can be used in this form for further batches. Compared with the known processes, in which the amine is recovered from the effluent in moderate yields by addition of alkali followed by extraction and fractional distillation of the extracts, a procedure which is fraught with losses, the present process provides a considerable improvement. Since the entire work-up procedure is carried out without water the yields are often also improved.

Having generally described this invention, a further understanding can be obtained by reference to certain specific examples which are provided herein for purposes of illustration only and are not intended to be limiting unless otherwise specified.

EXAMPLES

Example I: 2,4-dichloropyrimidine

A mixture of 112.1 g (1 mol) of uracil, 27.5 g (0.20 mol) of triethylamine hydrochloride and 460 g (3 mol) of POCl$_3$ was heated slowly to an internal temperature of from 110° to 120° C. and was maintained at that temperature for two hours. The reaction mixture was then cooled to about 30° to 40° C. and added dropwise at 50° C. over the course of 60 min. to a suspension of 416.5 g (2 mol) of PCl$_5$ in 200 ml of POCl$_3$, after which it was allowed to react at from 50° to 60° C. for a further 30 min. The POCl$_3$ was subsequently removed by distillation at 200 hPa on a 20 cm packed column. 350 g of ethyl acetate were added at 65° C. to the resulting mixture of 2,4-dichloropyrimidine and triethylamine hydrochloride, and the mixture was heated at reflux for several minutes and then filtered at room temperature. The triethylamine hydrochloride was washed three times with 100 ml (90 g) of ethyl acetate and then dried briefly at 60° C. and 200 hPa; yield: 24.3 g. The ethyl acetate was removed from the combined extracts by distillation on a 20 cm packed column; yield: 578 g (93.2%). The 2,4-dichloropyrimidine which remained was distilled at 40 hPa on an air-cooled distillation bridge; yield: 136.6 g (91.7%).

Example 2: 4,6-dichloropyrimidine 127.2 g (1 mol) of N,N-dimethylcyclohexylamine were added dropwise at from 50° to 60° C. over the course of 60 min. to 112.1 g (1 mol) of 4,6-dihydroxypyrimidine and 460 g (3 mol) of POCl₃, and the mixture was then heated at from 95° to 100° C. for 3 h. Subsequently 416.5 g (2 mol) Of PCl₅ were added at from 50° to 60° C. over the course of 90 min. and the mixture was allowed to react for a further 60 min. POCl₃ was then distilled off at 200 hPa on a 20 cm packed column. 355 g of 1-chlorobutane were added at 65° C. to the resulting mixture of 4,6-dichloropyrimidine and N,N-dimethylcylcohexylamine hydrochloride, and the mixture was heated at reflux for 60 min. It was then filtered at room temperature. The hydrochloride was washed three times with 100 ml (=88.4 g) of 1-chlorobutane; moist yield: 210.8 g. After the product was dried at 100° C. and at atmospheric pressure, 163.7 g (100%) of hydrochloride and 32 g of 1-chlorobutane were obtained. The 1-chlorobutane was removed from the extracts by distillation at atmospheric pressure on a 20 cm packed column; yield: 580.8 g (93.7%). 40 g of diphenyl carbonate as distillation auxiliary were added to the crude 4,6-dichloropyrimidine. Distillation was then carried out at about 150 hPa on a distillation bridge heated at 70° C. After a small initial fraction, 129.3 g (86.8%) of pure 4,6-dichloropyrimidine were obtained, with a boiling range of 120° to 125° C.

Example 3: 4,6-dichloropyrimidine 112.1 g (1 mol) of 4,6-dihydroxypyrimidine were metered at 80° C. into 180.1 g (1—1 mol) of N,N-dimethylcyclohexylamine hydrochloride (of which 163.7 g were obtained from Example 2 and 16.4 g were fresh product) and, likewise recovered from Example 2, 460 g (3 mol) of POCl₃, and the mixture was heated at from 95° to 100° C. for 3 h. Subsequently the procedure of Example 2 was followed. Using 1-chlorobutane recovered from Example 2, 178.7 g (99.2%) of hydrochloride and 128.1 g (86.0%) of 4,6-dichloropyrimidine were obtained.

Example 4: 4.6-dichloropyrimidine 112.1 g (1 mol) of 4,6-dihydroxypyrimidine were metered at 80° C. into 137.65 g (1 mol) of triethylamine hydrochloride and 460 g (3 mol) of POCl₃, and the mixture was heated at from 95° to 100° C. for 3 h. The procedure of Example 2 was then followed. However, the resulting mixture of 4,6-dichloropyrimidine and triethylamine hydrochloride was admixed at from 70° to 80° C. with 400 g of a mixture of equal parts by weight of 1,3,5-trimethylbenzene and p-tert-butyltoluene and was stirred at 80° C. for 15 min.

The mixture was then filtered at room temperature, the solid washed three times with 150 g of the above-mentioned mixture, and the triethylamine hydrochloride was dried at 100° C. and 13 hPa; yield: 135.6 g (98.5%). The combined filtrates and washing liquors were distilled at from 75° to 95° C. and at from 30 to 365 hPa; distillate: 980 g of solution containing 12.6% of 4,6-dichloropyrimidine, corresponding to a yield of about 83.

Example 5: 2,4-dichloro-5-methylpyrimidine

A mixture of 126.1 g (1.0 mol) of thymine, 27.5 g (0.20 mol) of triethylamine hydrochloride and 460 g (3 mol) of POCl₃ was heated slowly to an internal temperature of from 108° to 110° C. and was maintained at that temperature for 3 hours. 416.5 g (2 mol) of PCl₅ were then metered in slowly using a screw at 50° C. over the course of 60 min. The mixture was subsequently allowed to react for a further 30 min. at from 50° to 60° C. The subsequent work-up procedure was as for Example 1, except for using 200 g of n-hexane instead of 350 g of ethyl acetate. Recovered triethylamine hydrochloride: 27.2 g (98.9%), yield of 2,4-dichloro-5-methylpyrimidine: 149.2 g (91.5%), boiling range: 138° to 145° C. at 27 hPa.

Example 6: 2-phenyl-4,6-dichloropyrimidine 37.6 g (0.2 mol) of 2-phenyl-4,6-dihydroxypyrimidine were added in portions at 80° C. to 92.0 g (0.6 mol) Of POCl₃ and 27.5 g (0–2 mol) of triethylamine hydrochloride and the mixture was then heated at an internal temperature of 110° C. for 2 h. The subsequent reaction with 83.3 g (0.4 mol) of PCl₅ and the distillative removal of the POCl₃ are carried out as in Example 2. 90 g of ethyl acetate were added at 60° C. to the residue and the mixture stirred for 30 min. In analogy to Example 1, 27.3 g (99.2%) of triethylamine hydrochloride were recovered. The residue obtained after distillative removal of the ethyl acetate was recrystallized from methanol; yield: 35.8 g (79.6%), melting point: 95° to 96° C.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the U.S. is:

1. A process for the preparation of chloropyrimidines of the formula

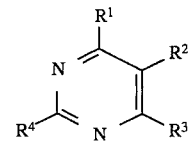

wherein the substituents $R^1$, $R^2$, $R^3$ and $R^4$ are hydrogen, alkyl, cycloalkyl, aryl, heteroaryl, $OR^5$, $SR^5$, $NH_2$, $NHR^5$, $N(R^5)_2$, NO, $NO_2$, COOH, $COOR^5$, CN or halogen, where $R^5$ may be alkyl, cycloalkyl, aryl or heteroaryl but at least one of the substituents $R^1$ to $R^4$ must be Cl, comprising:

reacting a hydroxy-pyrimidine or its tautomeric keto form with phosphoryl chloride in the presence of an amine or amine hydrochloride;

recovering phosphoryl chloride after the reaction by adding phosphorus pentachloride and distilling the phosphoryl chloride; and separating the chloropyrimidine from the amine hydrochloride by addition of a solvent which will dissolve the chloropyrimidine but not the amine hydrochloride and removing the amine hydrochloride, wherein said solvent is a member selected from the group consisting of esters having a total of 2 to 10 carbon atoms, aliphatic hydrocarbons of 6 to 14 carbon atoms, aromatic hydrocarbons of 6 to 14 carbon atoms, halogenated hydrocarbons of 1 to 6 carbon atoms, ethers of 4 to 12 carbon atoms and mixtures thereof.

2. The process according to claim 1, wherein said solvent is added after the distillation of the phosphroryl chloride.

3. The process according to claim 1, wherein said amine or amine hydrochloride is an aliphatic amine.

4. The process according to claim 1, wherein said amine or amine hydrochloride is a member selected from the group consising of aliphatic tertiary amines $N(R^6)$, and the corresponding amine hydrochlorides $N(R^6)H^+Cl^-$ wherein $R^6$ is a straight-chain or branched alkyl of 1 to 8 carbon atoms or is cycloalkyl of 5 to 8 carbon atoms.

5. The process according to claim 1, wherein said amine or amine hydrochloride is employed in an amount of from 0.1 to 2.0 mol per mol of hydroxypyrimidine.

6. The process according to claim 1, wherein said amine hydrochloride which is removed is recycled to said reacting step.

7. The process according to claim 1, wherein said amine hydrochloride is removed from said chloropyrimidine by filtration.

8. The process according to claim 1, wherein said amine hydrochloride is removed from said chloropyrimidine by centrifugation.

9. A process for the preparation of chloropyrimidines of the formula

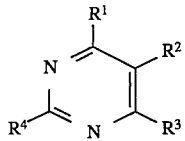

wherein the substituents $R^1$, $R^2$, $R^3$ and $R^4$ are hydrogen, alkyl, cycloalkyl, aryl, heteroaryl, $OR^5$, $SR^5$, $NH2$, $NHR^5$, $N(R^5)_2$, NO, $NO_2$, COOH, $COOR^5$, CN or halogen, where $R^5$ may be alkyl, cycloalkyl, aryl or heteroaryl but at least one of the substituents $R^1$ to $R^4$ must be Cl, comprising:

reacting a hydroxy-pyrimidine or its tautomeric keto form with phosphoryl chloride in the presence of an amine or amine hydrochloride;

recovering phosphoryl chloride after the reaction by adding phosphorus pentachloride and distilling the phosphoryl chloride; and separating the chloropyrimidine from the amine hydrochloride by addition of a solvent which will dissolve the chloropyrimidine but not the amine hydrochloride and removing the amine hydrochloride, wherein said solvent is a member selected from the group consisting of esters having a total of 2 to 10 carbon atoms, aliphatic hydrocarbons of 6 to 14 carbon atoms, aromatic hydrocarbons of 6 to 14 carbon atoms, halogenated hydrocarbons of 1 to 6 carbon atoms, ethers of 4 to 12 carbon atoms and mixtures thereof, wherein said separating step provides a solution of chloropyrimidine and solvent, which is then distilled to separate the chloropyrimidine from the solvent, wherein high-boiling liquids or low-melting solids are added as distillation auxiliaries.

* * * * *